United States Patent [19]

McCauley et al.

[11] Patent Number: 5,652,365
[45] Date of Patent: Jul. 29, 1997

[54] PROCESS FOR THE PRODUCTION OF FINASTERIDE

[75] Inventors: James A. McCauley, Belle Meade; Richard J. Varsolona, Scotch Plains, both of N.J.

[73] Assignee: Merck & Co., Inc., Rahway, N.J.

[21] Appl. No.: 411,685

[22] PCT Filed: Nov. 5, 1993

[86] PCT No.: PCT/US93/10659

§ 371 Date: Mar. 30, 1995

§ 102(e) Date: Mar. 30, 1995

[87] PCT Pub. No.: WO94/11387

PCT Pub. Date: May 26, 1994

Related U.S. Application Data

[63] Continuation-in-part of Ser. No. 10,734, Jan. 29, 1993, Pat. No. 5,468,860, which is a continuation-in-part of Ser. No. 978,535, Nov. 19, 1992, abandoned.

[51] Int. Cl.$^6$ .................................................. C07J 73/00
[52] U.S. Cl. .................................................. 546/77
[58] Field of Search .................................................. 546/77

[56] References Cited

U.S. PATENT DOCUMENTS

| | | | |
|---|---|---|---|
| 4,760,071 | 7/1988 | Rasmusson | 546/77 |
| 5,021,575 | 6/1991 | King et al. | 546/77 |
| 5,061,801 | 10/1991 | Williams et al. | 546/77 |
| 5,084,574 | 1/1992 | Bhattachrya et al. | 546/77 |
| 5,237,061 | 8/1993 | Bhattachrya et al. | 546/77 |

FOREIGN PATENT DOCUMENTS

| | | |
|---|---|---|
| 0 298 652 | 1/1989 | European Pat. Off. . |
| 0 367 502 | 5/1990 | European Pat. Off. . |
| 0 428 366 | 5/1991 | European Pat. Off. . |
| 0 461 930 A1 | 12/1991 | European Pat. Off. . |
| 462662 | 12/1991 | European Pat. Off. . |
| 0 478 066 | 4/1992 | European Pat. Off. . |
| 0 478 065 | 4/1992 | European Pat. Off. . |
| 0 599 376 A2 | 6/1994 | European Pat. Off. . |
| 0 655 459 A2 | 5/1995 | European Pat. Off. . |
| 94-11387 | 5/1994 | WIPO .................................................. 546/77 |

OTHER PUBLICATIONS

Levin et al., Synthetic Comm. 12(13), pp. 989–993 (1982), "An Alternative Procedure for the Aluminum–Mediated Coversion of Esters to Amides".
Evanseck et al., J. Am. Chem. Soc. 109, pp. 2349–2353 (1987), "Ab Initio Study of the SN2 Reactions of OH– and OOH– with CH3Cl".
Merck Index, 10th Ed., Merck & co., Inc, Rahway, NJ. 1983 p. ONR 13 Bhattachrya, Synthetic Comm. 20(17) pp. 2683–2690 (1990).
McCauley, ALChE Symposium Series, Particle Design via Crystallization, vol. 87 (No. 284) 1991 pp. 58–63.
The Daily (Tuesday, May 7, 1996), "New Data on Proscar, Abbott's Hytrin Show Conflicting Results".
Wall Street Journal (Tuesday, May 7, 1996), "Study Finds Abbott's Prostate Drug is Much More Effective than Merck's", p. B4.
US News & World Report, May 20, 1996, "Zapping a problem prostate".
Bodroux, Bull. Soc. Chem., France 33, 831 (1905), "Nouvelle methode de preparation des anilides".
Bodroux, Bull. Soc. Chem., France 35, 519 (1906), "Action des ethers chloracetiques sur les derives halogeno–magnesiens de l'ortholuidine".
Bodroux, Bull. Soc. Chem., France 1, 912(1907).
Bodroux, Compt. Rend., vol. 138, p. 1427 (1904), "Chimie Organique: Nouvelle methode de preparation des anilides".
Bodroux, Compt. Rend., vol. 140, 1108 (1905), "Chimie Organique: Mode de formation de quelques derives mono-substitutues de l'urethane".
Bodroux, Comp. Rend., vol. 142, 401–2 (1906), "Chimie organique: Action de quelques ethers d'acides bibasiques sur les derives halogeno–magnesiens des amines aromatiques premaires".
Bhattacharya, Synthetic Comm., vol. 30 (17), pp. 2683–2690 (1990), "Acylimidazolides as versatile synthetic intermediates for the preparation of sterically congested amides and ketones: A practical synthesis of Proscar®".
McCauley, ALChE Symposium Series: Particle Design via Crystallizations, vol. 87 (284), pp. 58–63 (1991) "Detectionand Characterization of Polymorphism in the Pharmaceutical Industry".
Eaton et al., Jour. Am. Chem. Soc., vol. 111, pp. 8016–8018 (1989), "Magnesium Amide Bases and Amido–Gingnad 1. Ortho Magnesium".
Bhattacharya et al., Chem. Abstracts, vol. 114, Abstract No. 164608c (1990) "Acyl imidazolides as versatile synthetic intermediates for the preparation of sterically congested amides and ketones: a practical synthesis of Proscar".
Bhattacharya et al., Chem. Abstracts, vol. 113, Abstract No. 132584e, "Preparation of 4–azo–chol–1–ene–3,20–dione derivatives as testosterone reductase inhibitors".

*Primary Examiner*—Donald G. Daus
*Attorney, Agent, or Firm*—Catherine D. Fitch; Melvin Winokur

[57] ABSTRACT

A process for producing polymorphic Form I of finasteride, 17B-(N-tert-butyl carbamoyl)-4-aza-5α-androst-1-en-3-one, in substantially pure form comprising the steps of: (1) crystallization from a solution of finasteride in a water immiscible organic solvent and 0% or more by weight of water, producing solvated and non-solvated finasteride in solution, such that the amount of organic solvent and water in the solution is sufficient to cause the solubility of the non-solvated form of finasteride to be exceeded and the non-solvated form of finasteride to be less soluble than any other form of finasteride in the organic solvent and water solution: (2) recovering the resultant solid phase; and (3) removing the solvent therefrom; wherein the water immiscible organic solvent is ethyl acetate or isopropyl acetate and the amount of water in the solvent mixture is below 4 mg./ml.

2 Claims, No Drawings

PROCESS FOR THE PRODUCTION OF FINASTERIDE

CROSS REFERENCE TO RELATED APPLICATIONS

This application is the national phase application of PCT application Ser. NO. PCT/US93/10659, filed Nov. 5, 1993 and is a continuation-in-part of U.S. patent application Ser. No. 010,734, filed Jan. 29, 1993, and allowed and U.S. Pat. No. 5,468,860, which, in turn, is a continuation-in-part of U.S. patent application Ser. No. 978,535, filed Nov. 19, 1992, now abandoned.

BACKGROUND OF THE INVENTION

Finasteride, marketed under the tradename of PROSCAR®, by Merck & Co., Inc. is 17β-(N-tert-butyl carbamoyl)-4-aza-5α-androst-1-en-3-one and is a 5α-reductase inhibitor for use in treating acne, female hirsutism, and particularly benign prostatic hyperplasia. See U.S. Pat. No. 4,760,071 (1988), the entire disclosure of which is incorporated herein by reference.

The synthesis of finasteride in U.S. Pat. No. 4,760,071 involves reacting the 17β-(2-pyridylthio)carboxylate of 4-aza-5α-androst-1-ene-3-one with t-butylamine. A further synthesis of finasteride is described in Synthetic Communications, 30 (17), p. 2683–2690 (1990), the entire disclosure of which is incorporated herein by reference including the reacting of the 17-acylimidazole of 4-aza-5α-androst-1-ene-3-one with t-butylamine.

However, both of these reactions require the use of heterocyclic aromatic amines which are expensive and give rise to environmental safety and toxicity considerations. Both of these intermediates are prepared from the 17β-carboxylic acid.

The Bodroux reaction, described by F. Bodroux in the references, Bull. Soc. Chim. France 33, 831 (1905); 35, 519 (1906); 1, 912 (1907); Compt. Rend. 138, 1427 (1904); 140, 1108 (1905); 142, 401 (1906) discloses the reaction of the magnesium halide salts of amines with esters. However, there is no description or teachings that the reaction can be applied to the reaction of a sterically hindered amine, e.g. t-butyl amine, with a sterically hindered ester such as 1.

What is desired in the art is a method of synthesis of finasteride, which is environmentally safe and non-toxic, and does not utilize an aromatic heterocyclic amine. Preferably, the starting compound could be the 17-beta ester, (1) which would eliminate one step of the process in producing the above heterocyclic intermediates.

SUMMARY OF THE INVENTION

By this invention, there is provided a process for producing finasteride 2

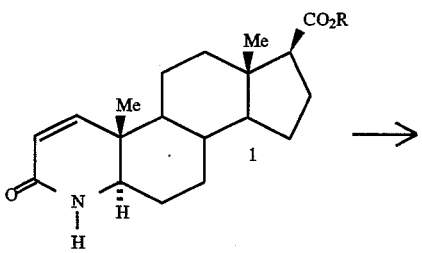

→

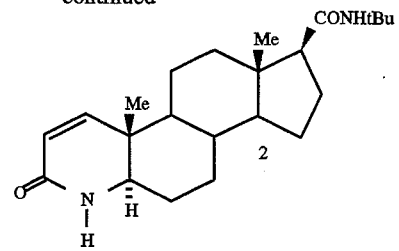

wherein R is $C_1$–$C_{10}$ linear, branched or cyclic alkyl, unsubstituted or substituted with one or more of phenyl, comprising the steps of:

(1) contacting the ester 1 with t-butylamino magnesium halide, wherein the molar ratio of t-butylamino magnesium halide to ester is at least about 2:1, in an inert organic solvent under an inert atmosphere;

(2) maintaining the reaction mixture at it temperature of at least 10° C.; and (3) recovering the product finasteride 2.

Also provided are intermediate compounds useful for the synthesis of finasteride. There is additionally provided a method for the synthesis, including separation and crystallization, of certain polymorphic crystalline forms of finasteride, as well as the polymorphic forms themselves.

DETAILED DESCRIPTION OF THE INVENTION

We have discovered that the 17β-carboalkoxy ester of 4-aza-5-alpha-androst-1-en-3-one (1) can be reacted with t-butyl amine together with an aliphatic/aryl magnesium halide reagent, e.g. ethyl magnesium bromide, where the magnesium halide reagent and t-butyl amine are present in at least about a 2:1 molar ratio to the ester (1), to produce finasteride (2) in good yield. The reaction between the aliphatic/aryl magnesium halide and t-butylamine produces t-butylamino magnesium halide. One mole of t-butylamino magnesium halide may be employed for the deprotonation of the ester A-ring lactam thereby solubilizing the steroid, a second mole required for the amidation reaction, and a third mole can be used for the deprotonation of the newly-formed amide. Alternatively, the ester (1) can be deprotonated with a Grignard reagent separately and then reacted with two moles of t-butylamino magnesium halide to undergo the amidation process.

In another alternative, the t-butylamino magnesium halide can be first preformed at ambient temperature in the same or separate vessel and then contacted with the 4-aza-steroid ester 1 in at least a 3:1 molar ratio of halide reagent:ester, preferably followed by heating up to, e.g., about 100° C. As a further alternative, the t-butyl magnesium halide can be formed in the same or a separate vessel in a 2:1 molar ratio to the ester 1, and then contacted with the ester 1 which has been previously contacted with the same or different Grignard reagent in a 1:1 molar ratio to deprotonate and solubilize the ester.

In one particular embodiment of this invention, a process for producing finasteride 2 comprises the steps of:

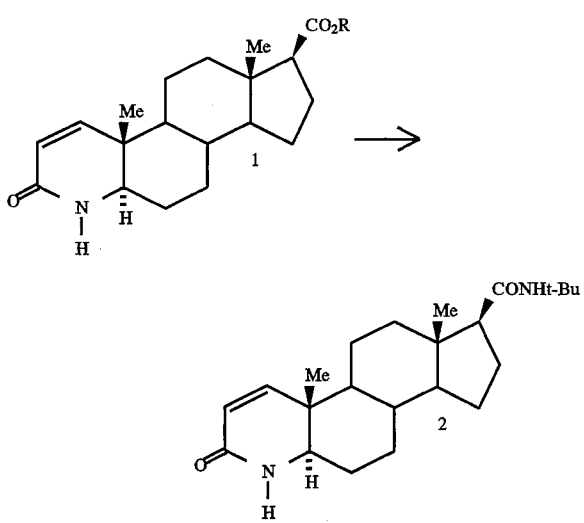

(1) contacting in one vessel the 4-aza-steroid ester 1 with t-butyl amine and aliphatic/aryl magnesium halide in an inert organic solvent under an inert atmosphere at a temperature in the range of −20° to 10° C., stirring the reaction mixture to produce the t-butyl magnesium halide in situ, in at least a 3:1 molar ratio to the ester 1, without reacting the ester with the aliphatic/aryl magnesium halide to form undesired corresponding ketone and alcohol products, (2) heating the reaction to 15° C. to 100° C. to react the ester with the t-butyl amino magnesium halide, and (3) recovering said product finasteride 2(where t-Bu indicates tertiary butyl).

The intermediate magnesium halide salt of the 4-aza-steroid 1 has the following formula:

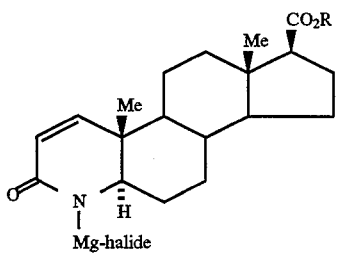

wherein R is $C_1$–$C_{10}$ linear, branched or cyclic alkyl, unsubstituted or substituted with one or more of phenyl.

The starting ester 1 and its synthesis are described in U.S. Pat. No. 4,760,071. The compound used to make 1 is the known steroid ester that is saturated at the 1,2 position, which is dehydrogenated with a dehydrogenating agent such as benzeneselenic anhydride in refluxing chlorobenzene.

The starting ester may-be the compound in which R is a $C_1$–$C_{10}$ linear, branched or cyclic alkyl, wherein the alkyl chain may be optionally substituted with one or more of phenyl. The ester moiety includes, e.g., methyl (Me), ethyl (Et), propyl, butyl, pentyl, hexyl, heptyl, octyl, nonyl, decyl, iso-propyl (i-Pr), iso-butyl (i-Bu), tert-butyl (t-Bu), sec-butyl (s-Bu), iso-pentyl, cyclohexyl and the like, and benzyl, —$CH_2CH_2$-phenyl, —$CH_2CH_2CH_2$-phenyl, and the like. R is particularly a straight chain alkyl which is unsubstituted or mono-substituted with phenyl, and more particularly methyl. Longer chain alkyl groups may be used as well, but are not required.

The t-butyl amine and aliphatic/aryl magnesium halide are each used in at least a 3:1 molar ratio to the ester (1) to form a 3:1 molar ratio, and preferably 3.5:1 to 5.5:1 molar ratio, of t-butylamino magnesium halide to the ester (1), to ensure proper and complete conversion of (1) to (2) and to minimize impurities. The reaction can be visualized mechanistically as the reaction of 3 moles of t-butylamino magnesium halide, formed by the reaction between the aliphatic/aryl magnesium halide and t-butylamine, with one mole of the ester 1. Alternatively, the reaction can be viewed as two moles of t-butyl magnesium halide reacting With one mole of the ester (1) magnesium halide salt.

The aliphatic/aryl magnesium halide is conventional and can be selected where:

(1) the aliphatic/aryl portion is $C_1$–$C_{18}$ linear, branched or cyclic alkyl, e.g. methyl, ethyl, propyl, isopropyl, n-butyl, sec-butyl, t-butyl, hexyl, cyclohexyl, octyl, decyl, dodecyl, tetradecyl, octadecyl, benzyl, allyl, vinyl, ethynyl, and the like; and (2) the aryl portion is phenyl, or mono-, di- or tri-substituted phenyl, wherein the substituents can include $C_1$–$C_4$ alkyl, $C_1$–$C_4$ alkoxy, e.g. methyl, methoxy, fluoro, and the like.

The halide is chloride; bromide, fluoride or iodide, and particularly bromide or chloride, and more particularly bromide. Preferred is ethyl magnesium bromide. The term "aliphatic/aryl magnesium halide" encompasses aliphatic magnesium halide and aryl magnesium halide.

The inert solvent used is a conventional Grignard Solvent and can be a $C_4$—$C_8$ linear or cyclic ether, including diethyl-ether, di-n-butyl ether, dimethoxyethane, tetrahydrofuran, dioxane, and the like. The solvent should be dry under the reaction conditions, which are usually carried out under an inert atmosphere, e.g. dry nitrogen, with stirring.

The reaction is carried out initially at a temperature sufficient to obtain product formation, and can be run, for example between about −40° to 40° C., and more particularly at a reduced temperature, for example, from about −20° to 10° C., during:

(1) reaction of t-butylamine and aliphatic/aryl magnesium halide to form the t-butylamino magnesium halide, and (2) the reaction between the ester 1 and t-butyl amino magnesium halide (or a Grignard reagent) to form the magnesium halide salt of the ester 1.

Subsequently, the reaction mixture is stirred and maintained at a temperature sufficient to allow the amidation process to proceed. The reaction may generally be allowed to warm to a temperature of, for example, about 10° C. or up to room temperature, and it may be further heated to about 100° C., or up to the boiling point of the solvent. Generally the heating time is 2 to 12 hours.

Alternatively, the t-butylamino magnesium halide may be preformed, for example at ambient temperature, and subsequently reacted with the 4-aza-ester steroid (1) at ambient temperature.

Workup of the crude finasteride is conventional as well as the apparatus used to carry out the process. In general, chromatography on silica gel and/or crystallization from a suitable solvent, e.g. methylene chloride/ethyl acetate or acetic acid/water can serve to purify the finasteride.

The order of the addition of ester, t-butyl amine and aliphatic/aryl magnesium halide can be modified and reversed, if desired, with good results. Particularly, the t-butyl amine may be reacted first with the aliphatic/aryl magnesium halide to preform the t-butylamino magnesium halide prior to contacting the ester 1.

The following Examples are illustrative of the method claimed herein and should not be construed to represent limitations or restrictions on the scope or spirit of the invention as disclosed.

EXAMPLE 1

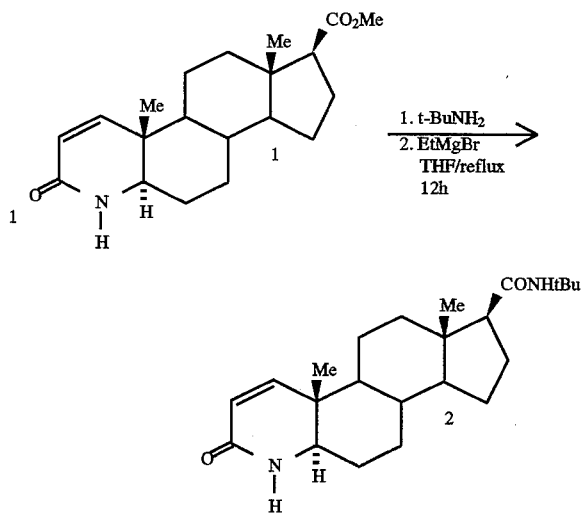

In a flask equipped with an overhead stirrer, a nitrogen inlet, and reflux condenser was placed 840 ml of dry THF and 20.0 g of $\Delta^1$-methyl ester (1). The resulting slurry was cooled to −5° to −10° C., and 27.6 mL of t-butylamine was added. A solution of ethylmagnesium bromide in THF (122 mL, 2M) was added maintaining the temperature of the reaction mixture below 10° C. The reaction was heated at reflux for 12 hours and was added to a cold (10° C.) solution of 25% ammonium chloride in water. The mixture was warmed to 25° C. and allowed to settle. The THF solution was separated and concentrated by atmospheric distillation to 200 mL and the product was crystallized by adding approximately 600 mL of dilute aqueous HCl. The resulting white solid was isolated by filtration and was dried at 70° C. under vacuum to give 21.7 g (97% yield) of finasteride. The product finasteride can be purified by conventional procedures, e.g. recrystallization from methylene chloride/ethyl acetate or acetic acid/water, mp. 261 ° C.

EXAMPLE 2

In a flask equipped with an overhead stirrer, a nitrogen inlet, and reflux condenser was placed 516 mL of dry THF and 27.6 mL of t-butylamine. The solution was cooled to 10° C. and 244 mL of 1M ethylmagnesium bromide in THF was added maintaining the reaction temperature below 30° C. A slurry containing 10.0 g of $\Delta^1$-methyl ester 1 in 100 mL of dry THF was added. The reaction was heated at reflux for 4–6 hours and was added to a cold (10° C.) solution of 25% ammonium chloride in water. The mixture was warmed to 25° C. and allowed to settle. The THF solution was separated and concentrated by atmospheric distillation to 200 mL and the product was crystallized by adding 200 mL of dilute HCl. The resulting white solid was isolated by filtration and was dried at 70° C. under vacuum to give 21.6 g (97% yield) of finasteride.

Polymorphism can be defined as the ability of the same chemical substance to exist in different crystalline structures. The different structures are referred to as polymorphs, polymorphic modifications or forms. Finasteride has been found to exist in at least two polymorphic nonsolvated forms, Form I and Form II, each of which can be formed by careful control of the crystallization conditions.

Polymorphic Form I can be prepared by:

(1) crystallization from a mixture of finasteride in an organic solvent and 0% or more by weight of water, such that the amount of organic solvent and water in the mixture is sufficient to cause the solubility of the non-solvated form of finasteride (Form I) to be exceeded and the non-solvated form of finasteride to be less soluble than any other form of finasteride in the mixture;

(2) recovering the resultant solid phase; and (3) removing the solvent therefrom.

Organic solvents useful in this process include any solvents that finasteride can be dissolved in. Some examples of organic solvents include, e.g., tetrahydrofuran (THF), organic acids, ethyl acetate (EtOAc), toluene, iso-propyl acetate, and the like. Furthermore, the organic solvent may be one that is known in the art as being water-miscible. The term "water-miscible" solvents, as used herein, is meant to include solvents which do not form a two-phase system with water under conditions sufficient to crystallize the instant polymorphs. For example, water-miscible solvents include but are not limited to THF, and the organic acids such as formic acid, acetic acid, propionic acid, and the like. Also, the organic solvent may be one that is known in the art as being water-immiscible. The term "water-immiscible" solvents, as used herein, is meant to include solvents which form a two-phase system with water under conditions sufficient to crystallize the instant polymorphs. For example, water-immiscible solvents include but are not limited to toluene, ethyl acetate, iso-propyl acetate and the like.

When water-miscible solvents are used in the above-described process, polymorphic Form I of finasteride can be produced by using relatively wet solvent mixture, e.g., when using glacial acetic acid, about 83 % or more by weight of water may be used to obtain Form I, at an ambient temperature of about 25° C.

When using organic solvents that are generally considered water immiscible, e.g., toluene, ethyl acetate, iso-propyl acetate and the like, the above described process for making Form I is carried out in relatively dry solvent. For example, to produce Form I of finasteride from an ethyl acetate/water mixture, the amount of water used is at most about 3.5 mg/ml, and from an iso-propyl acetate/water mixture, the amount of water used is at most about 1.6 mg/ml, both at an ambient temperature of about 25° C.

The crystallization examples above are for procedures conducted at ambient temperature. As can be appreciated by those skilled in the art, the mount of water needed to produce Form I in any given organic solvent mixture will vary with temperature, since changes in temperature will alter the solubility of the solute. For example, when using iso-propyl acetate to produce Form I, the following amounts of water may be present at the indicated temperatures:

| Temperature | Amount of Water |
| --- | --- |
| 1.4° C. | 0.8 mg/ml or less |
| 6° C. | 0.9 mg/ml or less |
| 12° C. | 1.0 mg/ml or less |
| 18° C. | 1.3 mg/ml or less |

Polymorphic Form I can also be prepared by heating polymorphic Form II of finasteride to at least about 25° C. in water or an organic solvent for a time sufficient to completely convert form II to form I, and recovering the resultant solid phase, e.g. by filtration.

Polymorphic Form II can be prepared by:

(1) crystallization from a mixture of finasteride in an organic solvent and water, such that the amount of organic solvent and water in the mixture is sufficient to cause the solubility of the solvated form of finasteride to be exceeded and the solvated form of finasteride to be less soluble than any other form of finasteride in the mixture;

(2) recovering the resultant solid phase; and (3) removing the solvent therefrom.

The organic solvents useful in this process are as described above, and likewise include water-miscible and water-immiscible solvents. However, when producing Form II from a water-miscible solvent, the weight percentage of water used in the solvent mixture will be less than that used to produce Form I from the same water-miscible solvent. For example, to produce Form II of finasteride from a glacial acetic acid/water mixture, the weight percentage of water in the solvent mixture is less than about 83%, at an ambient temperature of about 25° C.

Furthermore, when a water-immiscible solvent such as ethyl acetate or iso-propyl acetate is used to produce Form II, then the amount of water used in the solvent mixture will be more than that used to produce Form I from the same organic solvent. For example, to produce Form II of finasteride from an ethyl acetate/water mixture, the amount of water used is greater than about 3.5 mg/ml, and from an iso-propyl acetate/water mixture, the amount of water used is greater than about 1.6 mg/ml, both at an ambient temperature of about 25° C. As explained above, those skilled in the art will appreciate that changes in temperature may affect the amount of water needed to produce Form II from any given solvent mixture.

Polymorphic Form II can also be prepared by heating polymorphic Form I of finasteride to at least about 150° C. for a time sufficient to completely convert Form I to Form II, for example about an hour, and recovering the resultant solid phase.

The following Examples illustrate methods for obtaining polymorphic Forms I and II of finasteride (Proscar®, MK 906) and some characterization data. The following examples are provided to further illustrate details for the preparation of the compounds of the present invention. The examples are not intended to be limitations on the scope of the instant invention in any way, and they should not be so construed.

EXAMPLE 3

Finasteride Form I can be prepared by dissolving finasteride in glacial acetic acid (ca. 100 mg/ml) and adding water with stirring until the weight % of water equals or exceeds 84%. The resulting solid phase is collected by filtration and dried under vacuum and at about 50° C. The resulting Form I is characterized by a differential scanning calorimetry (DSC) curve, at heating rate of 20° C./min and in a closed cup, exhibiting a minor endotherm with a peak temperature of about 232° C., an extrapolated onset temperature of about 223° C. with an associated heat of about 11 joules/gm and by a major melting endotherm with a peak temperature of about of 261° C., an extrapolated onset temperature of about 258° C. with an associated heat of about 89 J/gm. The x-ray powder diffraction pattern is characterized by d-spacings of 6.44, 5.69, 5.36, 4.89, 4.55, 4.31, 3.85, 3.59 and 3.14. The FT-IR spectrum (in KBr) shows bands at 3431, 3237, 1692, 1666, 1602 and 688 cm−1. The solubilities in water and cyclohexane at 25° C. are 0.05+0.02 and 0.27+0.05 mg/gm respectively.

In addition, Form I of finasteride can be prepared by recrystallization from dry ($H_2O<1$ mg/ml) ethyl acetate and isopropyl acetate, at ambient temperature (~25° C.). The isolated solids are dried under vacuum at about 50° C. and have the same physical characterization data as given above.

In addition, Form I was prepared by stirring Form II overnight in dry toluene at ambient temperature, and recovering the resultant solid phase. Form I was also obtained by stirring Form II overnight in dry acetonitrile at ambient temperature, and recovering the resultant solid phase.

EXAMPLE 4

Form II of finasteride can be prepared by dissolving finasteride in glacial acetic acid (ca. 100 mg/ml) and adding water with stirring until the weight % of water equals about 75% but not in excess of 80%. The resulting solid phase is collected by filtration and dried under vacuum and at about 100° C. The resulting Form II is characterized by a DSC curve, at heating rate of 20° C./min and in a closed cup, exhibiting a single melting endotherm with a peak temperature of about of 261 ° C., an extrapolated onset temperature of about 258° C. with an associated heat of about 89 J/gm. The x-ray powder diffraction pattern is characterized by d-spacings of 14.09, 10.36, 7.92, 7.18, 6.40, 5.93, 5.66, 5.31, 4.68, 3.90, 3.60 and 3.25. The FT-IR spectrum (in KBr) shows bands at 3441, 3215, 1678, 1654, 1597, 1476 and 752 cm−1. The solubilities in water and cyclohexane at 25° C. are 0.16+0.02 and 0.42+0.05 mg/gm respectively.

In addition, Form II of finasteride can be prepared by recrystallization from ethyl acetate containing from about 3.5 to 30 mg/ml of water, or from isopropyl acetate containing from about 1.6 to 15 mg/ml of water, at ambient temperature (~25° C.). The isolated solids are dried under vacuum at about 80° C. and have the same physical characterization data as given above.

Form II can also be prepared by heating Form I up to about 150° C., holding for about one hour and cooling back to room temperature. The Form II prepared in this manner has the same physical characterization data as given above.

What is claimed is:

1. A process for producing polymorphic Form I of 17β-(N-tert-butyl carbamoyl)-4-aza-5α-androst-1-3-one in substantially pure form, comprising the steps of:

(1) crystallization from a solution of finasteride in a water immiscible organic solvent and 0% or more by weight of water, producing solvated and non-solvated finasteride in solution, such that the amount of organic solvent and water in the solution is sufficient to cause the solubility of the non-solvated form of finasteride to be exceeded and the non-solvated form of finasteride to be less soluble than any other form of finasteride in the organic solvent and water solution;

(2) recovering the resultant solid phase; and (3) removing the solvent therefrom;

wherein the water immiscible organic solvent is ethyl acetate and the amount of water in the solvent mixture is at most about 3.5 mg/ml.

2. A process for producing polymorphic Form I of 17β-(N-tert-butyl carbamoyl)-4-aza-5α-androst-1-en-3-one in substantially pure form, comprising the steps of:

(1) crystallization from a solution of finasteride in a water immiscible organic solvent and 0% or more by weight of water, producing solvated and non-solvated finasteride in solution, such that the amount of organic solvent and water in the solution is sufficient to cause the solubility of the non-solvated form of finasteride to be exceeded and the non-solvated form of finasteride to be less soluble than any other form of finasteride in the organic solvent and water solution;

(2) recovering the resultant solid phase; and (3) removing the solvent therefrom, wherein the water immiscible organic solvent is isopropyl acetate, and the amount of water in the solvent mixture is at most about 1.6 mg/ml.

* * * * *